United States Patent [19]
Boudewijn et al.

[11] Patent Number: 5,292,305
[45] Date of Patent: Mar. 8, 1994

[54] DOUBLE-LUMEN ANGIOSCOPY CATHETER

[75] Inventors: Alexander C. Boudewijn, La Leek; Gjalt Bosma, Ek Drachten, both of Netherlands

[73] Assignee: Cordis Corporation, Miami Lakes, Fla.

[21] Appl. No.: 938,620

[22] Filed: Sep. 1, 1992

[30] Foreign Application Priority Data

Sep. 10, 1991 [NL] Netherlands ............... 9101534

[51] Int. Cl.$^5$ .................................. A61M 3/00
[52] U.S. Cl. ........................... 604/43; 604/283; 128/6
[58] Field of Search .............. 604/43, 164, 167, 280, 604/283, 284; 128/4–6

[56] References Cited

U.S. PATENT DOCUMENTS

| | | | |
|---|---|---|---|
| 3,757,768 | 9/1973 | Kline . | |
| 4,424,833 | 1/1984 | Spector et al. | 604/167 |
| 4,619,643 | 10/1986 | Bai | 604/43 |
| 4,682,978 | 7/1987 | Martin | 604/283 |
| 4,736,733 | 4/1988 | Adair | 604/280 |
| 4,895,561 | 1/1990 | Mahurkar | 604/43 |
| 5,040,548 | 8/1991 | Yock | 128/898 |
| 5,059,170 | 10/1991 | Cameron | 604/43 |

FOREIGN PATENT DOCUMENTS 266928 5/1988 European Pat. Off. .
321614 6/1989 European Pat. Off. .
366794 5/1990 European Pat. Off. .

*Primary Examiner*—John D. Yasko
*Assistant Examiner*—Anthony Gutowski
*Attorney, Agent, or Firm*—Lockwood, Alex, Fitzgibbon & Cummings

[57] ABSTRACT

A double-lumen angioscopy catheter is provided which includes separate passageways for a guidewire and for an optic fiber bundle, which passageways are joined into a single tubular component for the portion of the catheter which enters the body. The passageways are separated from each other at the location external of the body whereby each of the guidewire and the optic fiber bundle can be inserted and removed in separate stages. An assembly can also be provided for passing flushing liquid through either or both of the passageways. The guidewire can be used to maneuver the distal end of the optic fiber bundle so as to accomplish controlled inspection within the body vessel. The angioscopy catheter facilitates a procedure whereby a single guidewire is inserted and remains in place throughout use of the angioscopy catheter, whether during pretreatment or posttreatment inspection. The same guidewire likewise remains in place and functions as a guidewire for a treatment catheter such as a percutaneous transluminal coronary angioplasty catheter.

7 Claims, 3 Drawing Sheets

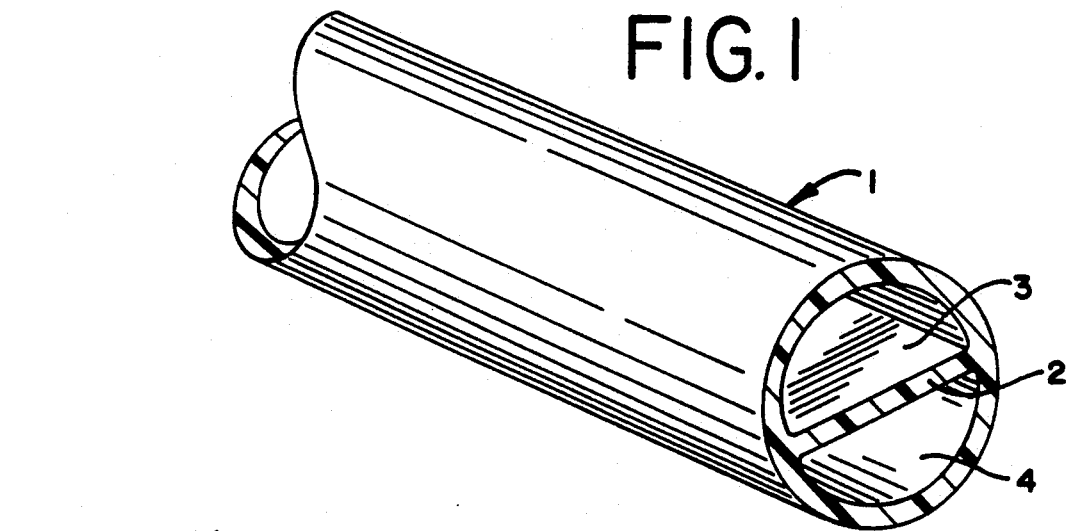
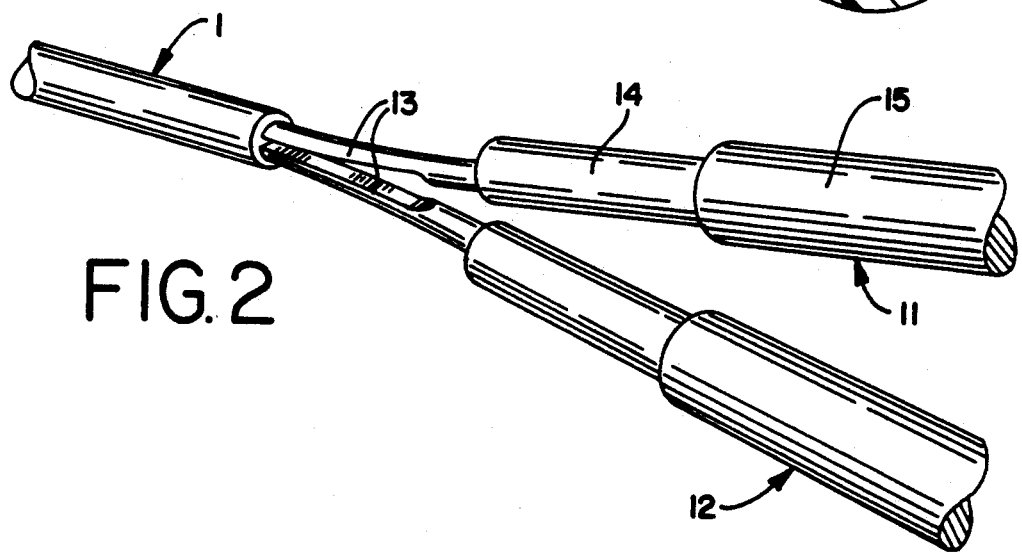
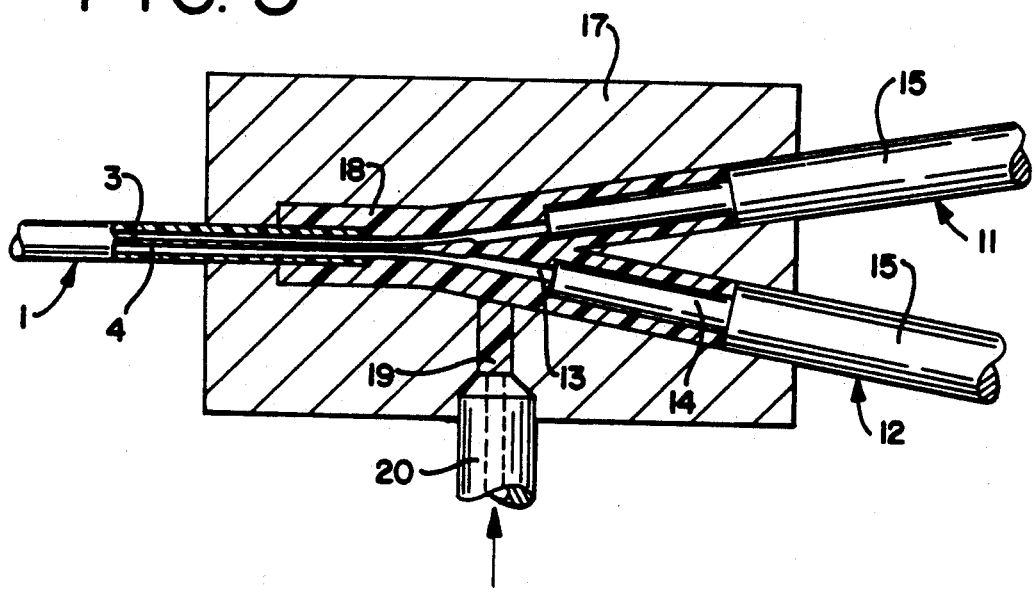

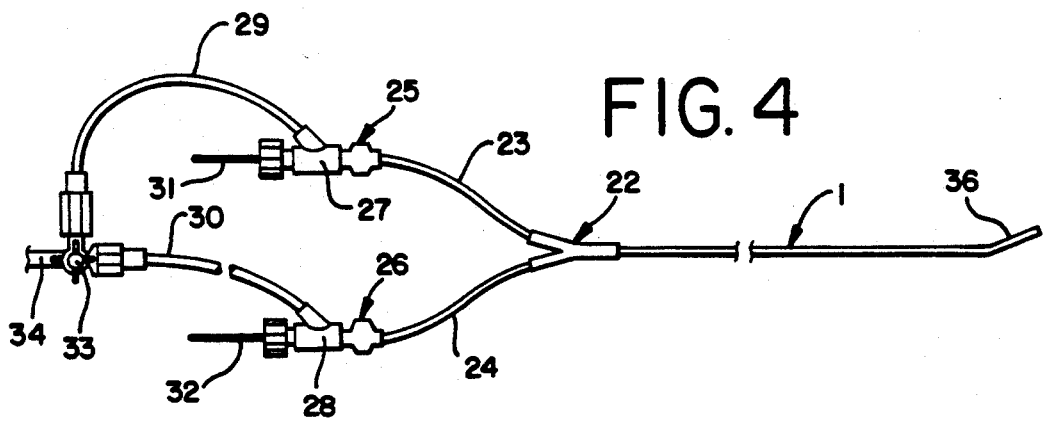
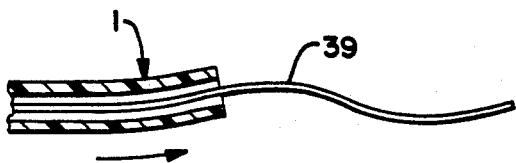
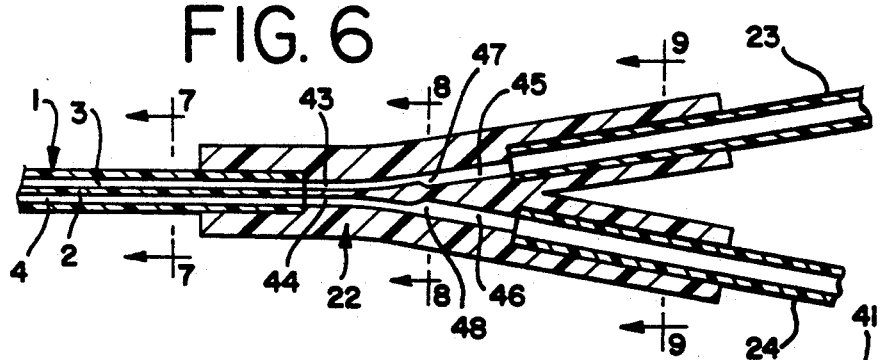
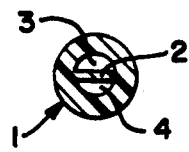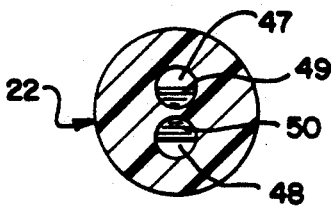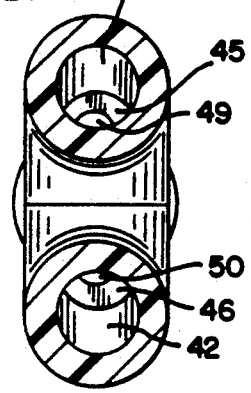

DOUBLE-LUMEN ANGIOSCOPY CATHETER

BACKGROUND AND DESCRIPTION OF THE INVENTION

The present invention generally relates to angioscopy catheters and procedures. More particularly, the invention relates to a double-lumen catheter which is particularly intended for angioscopic uses. During use, the two-channel or double-lumen portion of the catheter is inserted into a patient. One channel accommodates a guidewire, while the other channel accommodates an optic fiber bundle, in particular a fiber bundle of an endoscope. The guidewire and the optic fiber bundle are capable of being inserted into and pushed through their respective channels. The guidewire and the fiber bundle can be fed in and manipulated separately of one another by way of single-lumen portions of the catheter proximal of the double-lumen portion of the catheter. In a preferred aspect of the invention, the transition from the single-channel catheter portions to an intermediate fork piece and from the intermediate fork piece to the two-channel portion of the catheter is uniform, there being no internally protruding edges which could make difficult the introduction of the guidewire and/or the optic fiber bundle in either direction, that is either into the distal end (double-lumen portion) or into the proximal end (either single-lumen portion).

During angioplasty treatments and the like, procedures are known and used whereby a lesion is located by means of x-ray based procedures which utilize radiopaque dyes and instruments having radiopaque areas which provide an image to assist the surgeon in diagnosing and treating diseased areas by transluminal procedures. While these approaches have met with reasonable success, it is believed that improvements in diagnosis and treatment can be attained by being able to actually view the lesion or other diseased area, rather than be limited to only images created by radiopaque materials. Actual viewing, such as through an optic fiber bundle, provides a three-dimensional view allowing an assessment of characteristics of the diseased area that cannot be attained by way of radiopaque images. It is also generally desirable to be able to view the lesion or other treated area after treatment, as well as before treatment. A procedure such as angioscopy allows for a direct look at a stenosis with the objective of being able to see the kind of material the stenosis is comprised of.

As is the case for any inner luminal procedure, minimizing the number of insertions and withdrawals of implements within body vessels is an objective to be sought. Also, difficulties can arise in attempting to properly position optic fiber bundles within vessels, particularly steering movement of the distal tip of optic fiber bundles to direct the viewing path as desired. Another difficulty which can be associated with fiber optic bundles when used within body passageways such as blood vessels is the accumulation of vision-obscuring materials such as blood and the like along the viewing pathway of the optic fiber bundle.

It has been found that the double-lumen angioscopy catheter and method in accordance with the present invention achieve the advantages of being able to manipulate an optic fiber bundle so that it is properly guided to the desired location for actually viewing a lesion or other diseased area prior to and/or after treatment of the diseased area. Included are means for flushing vision-obscuring materials such as blood and the like away from the field of view of the optic fiber bundle. At the same time, the invention requires only a single insertion of a guidewire to and beyond the diseased area, which guidewire can remain substantially in place throughout the duration of the procedure.

In summary, the present invention achieves these objectives and provides advantageous results along these lines by providing and using a double-lumen angioscopy catheter having a length of double-channel tubing positioned distally of a fork member which thereby connects the double-channel tubing to lengths of single-channel tubing whereby the double-channel tubing can be positioned within the body while the lengths of single-channel tubing are accessible from outside of the body. By this arrangement, access is provided in the form of continuous, separate passageways which are preferably smooth-walled from the distal tip of the double-channel tubing to a proximal portion of each length of single-channel tubing. One of these continuous passageways accommodates a guidewire, while the other accommodates an optical fiber bundle. The procedure for using the device includes inserting the guidewire at a location to the diseased area, such as distally beyond a lesion and substantially maintaining the guidewire in place at this location within the body. The double-lumen angioscopy catheter is then passed over and slidably guided by the guidewire whenever viewing of the diseased area is desired. Guidewire arrangements with respect to the optical fiber bundle facilitate steering at the distal tip of the optic fiber bundle. Preferably, flushing means are provided whereby this viewing operation can be accompanied by flushing of blood and the like away from the viewing pathway of the fiber optic bundle. Furthermore, the guidewire is usable, with the angioscopic device having been removed, for guiding an angioplasty catheter to the location for treatment.

It is a general object of the present invention to provide an improved angioscopy catheter and method of its use.

Another object of the present invention is to provide an improved angioscopic catheter having a double-lumen structure for accommodating both a guidewire and an elongated optic member generally longitudinally adjacent to one another.

Another object of this invention is to provide an improved procedure for treating disease transluminally which permits an actual optic fiber viewing of the diseased area without requiring more than one insertion of a guidewire to the diseased area being treated.

Another object of this invention is a double-lumen angioscopy catheter and method for the production of a fork portion thereof which provides a uniform and smooth transition from single-channel parts to a two-channel catheter portion, without forming internally protruding edges along the transition area.

Another object of the present invention is to provide an assembly of a double-lumen angioscopy catheter having a guidewire with a curved portion at or near its distal or leading end whereby rotating the guidewire about its longitudinal axis orients the catheter, particularly the optic fiber bundle thereof in a desired direction.

Another object of the present invention is to provide means for the person administering treatment to see that the extremity of the double-lumen catheter is about to extend beyond the distal end of its guiding catheter.

These and other objects, features and advantages of this invention will be clearly understood through a consideration of the following detailed description.

BRIEF DESCRIPTION OF THE DRAWINGS

The invention will be further elucidated in the following description with reference to the annexed Figures.

FIG. 1 is a perspective view of a piece of a two-channel catheter basic material which is used in accordance with the present invention.

FIG. 2 is a perspective view illustrating a second step of a preferred method of manufacturing the catheter.

FIG. 3 is an elevational view, partially in cross section, showing a third step of the preferred manufacturing method.

FIG. 4 is a top plan view, partially broken away, of a double-lumen catheter in accordance with the invention including tubes, valves and stopcocks as accessory components of an angioscopy set.

FIG. 5 schematically illustrates an embodiment incorporating a guidewire having a curved distal end portion.

FIG. 6 is a longitudinal cross-sectional view through the branch member of the double-lumen catheter illustrating the transitional area.

FIG. 7 is a cross-sectional view along the line 7—7 of FIG. 6.

FIG. 8 is a cross-sectional view along the line 8—8 of FIG. 6.

FIG. 9 is a cross-sectional view along the line 9—9 of FIG. 6.

DESCRIPTION OF THE PARTICULAR EMBODIMENTS

Figure 10:
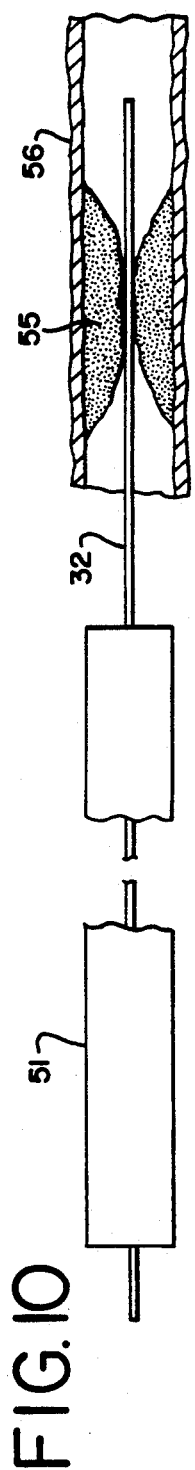
FIG. 10 is a generally schematic view illustrating an initial step in the procedure using the angioscopy catheter according to the invention.

A double-lumen angioscopy catheter is generally shown in FIG. 4. Its basic material parts include a two-channel tube-like member, generally designated as 1, and single-channel tube-like members 23, 24, the members 1, 23 and 24 being joined together by a fork piece or member 22. The configuration of the two-channel member 1 is illustrated in FIG. 1. Included are two parallel channels 3 and 4 mutually separated by a dividing wall 2.

These channels preferably have a D-shaped cross-section, as can be seen in FIG. 1. The D-shape is preferred because it provides the largest possible cross-sectional area for flushing. The channels 3, 4 are longitudinally adjacent to one another throughout the length of the two-channel member 1. The resultant "double" D-shaped configuration provides separate lumens for a guidewire and for a fiber bundle which avoids twisting of them with respect to each other.

It will be appreciated that the longitudinally adjacent channels 3 and 4, which are each typically D-shaped, communicate with lumens 41 and 42 of the single-channel catheter members 23, 24, respectively (FIG. 6 and FIG. 9). The fork piece 22 has a passageway which provides a transitional portion which gradually changes in shape between that of the parallel channels 3, 4 and that of the lumens 41, 42. FIGS. 6 through 9 illustrate the transitional portion in greater detail. The transitional portion includes two separate channels. Each channel includes a distal portion 43, 44 which typically has a generally D-shaped cross-section and a proximal portion 45, 46 which typically has a circular cross-section. Each transitional portion has a transitional zone 47, 48 having a tapered surface 49, 50 by which the proximal portion 45, 46, is transformed in shape to the distal portion 43, 44. The transitional portion thereby provides a gradual, uniform passageway without internally protruding edges which render difficult the introduction of devices therethrough such as guidewires and fiber bundles.

A better understanding of the structure of the angioscopy catheter in general and of the fork piece in particular can be gained by considering a method and device by which this structure can be manufactured. By this approach, core wires, generally designated 11, 12, are inserted into the end parts of the channels 3, 4 as shown in FIG. 2 and FIG. 3. Each of these core wires 11, 12 has a first portion 13 with a diameter length which is slightly larger (for example by about 0.1 mm) than the diameter length of the channels 3, 4 so that these first portions of the core wires 11, 12 slightly expand the double-lumen basic material 1 when inserted thereinto.

Each core wire 11, 12 further includes a second portion 14 having a diameter substantially equal to that of the single channel catheter tube-like material 23, 24, which will form a continuous connection with one of the channels 3, 4 of the two-channel tube-like member 1. Situated between the first portion 13 and second portion 14 is a transitional portion, the sectional shape of which gradually changes from that of the first portion to that of the second portion as generally described herein. Each core wire 11, 12 moreover has an end part or fixing part 15 which is intended for fixing in a mold 17.

Mold 17, which is illustrated schematically in FIG. 3, has a Y-shaped mold cavity 18 recessed into the mold 17. A proximal end part of the two-channel member 1 is received close to the stem of the "Y" with the first portions of the core wires 11, 12 inserted into the channels 3, 4. The fixing parts 15 of the core wires 11, 12 are clamped in the extensions of the arms of the "Y". As can be seen in FIG. 3, the mold cavity 18 generally defines the fork piece 22 wherein a channel connecting precisely onto the end parts of the channels 3, 4 is recessed by the first portions 13 of the core wires 11, 12, which channel transposes into a wider portion which is defined by the second portions 14 and into which distal end portions of the single-channel catheter tubing 23, 24 (FIG. 4) are fixed, for example by the use of an adhesive or glue or by other suitable procedure. Owing to the transition defined by the transitional portion of the core wires, the channels of the single-channel catheter members 23, 24 connect precisely, and without abrupt transition, onto the channels in the fork piece 22 recessed by the first portions 13 of the core wires 11, 12.

Mold 17 is further provided with a feed channel 19 onto which a nozzle 20 of an injection molding machine can connect. A suitable plastic such as a thermoplastic polymer is injected by way of nozzle 20 into the mold cavity 18. After injection and curing are completed, the plastic forms the fork piece 22.

End parts 13 of the core wires 11, 12 are preferably made of flexible material, such as spring steel. The end wires can thereby easily be removed after the formed assembly has been taken out of the mold 17. After removal of the core wires 11, 12, the single-channel catheter members 23, 24 are fixed into the fork piece 22. Preferably, connecting members, generally designated 25, 26 in FIG. 4, are fastened, for example by glue, adhesive or other suitable means, to the respective proximal ends of the single-channel catheter members 23, 24.

The method for manufacturing the double-lumen catheter according to this invention thus includes providing of piece of tube-like catheter material having two parallel, mutually separated lengthwise channels and providing two pieces of tube-like catheter material each having one lengthwise channel. Two core wires are used, each with a first portion closely fitting in the channels of the two-channel material and a second portion having a cross-section substantially corresponding to the external cross-section of the single-channel member. Each core wire has a transitional portion positioned therebetween, the shape of a section of which gradually transposes from that of the first portion to that of the lengthwise channel of the single-channel tubing member. The first portion of each core wire is inserted into each channel in the end part of the two-channel tubular member. A mold having a Y-shaped molding cavity is provided with a fixing means for enclosed receiving of the end part of the two-channel basic material close to the foot of the "Y" and with fixing means for enclosed Receiving of the second portion of the core wires close to the ends of the arms of the "Y". The end part of the two-channel tubular member is received into the mold with the core wires inserted therein. Thereafter, the mold cavity is filled with a curable material which forms a fork piece upon removing the thus formed assembly from the mold cavity after the curable material has hardened. Next, the core wires are removed from the fork piece, and the single-channel tubular members are fixed in the cavities in the fork piece defined by the second portions of the core wires. The other ends of the single-channel tubular material are fixed to connecting members that can allow passage, respectively, of a guidewire 32 and of an optic fiber bundle 31.

In a preferred embodiment of the manufacturing method, the core wires are selected in which the first portion has a diameter larger than the lengthwise channels of the two-channel member, the size being preferably about 0.1 mm larger. By thus providing the core wires in a diameter size slightly larger than the channels, the material is slightly expanded when the core wires are inserted so that a close-fitting engagement is obtained on the core wires. A very smooth transition is thus obtained after the injection molding of the fork piece 22.

It is also preferred that the core wires are selected such that the first portion of the transitional portion is elastically flexible. In this arrangement, when the core wires are pulled out of the formed fork piece, they deform elastically when following the channel formed in the fork piece by the first portion of the core wire, so that the core wires can be taken out easily. When the core wires are selected so that the first portion and the transitional portion are manufactured from spring steel, repeated use is made possible.

Optic fiber bundle 31 of an endoscope can be introduced via the channel that is accessible by way of the connecting member 25. For this purpose, the connecting member 25 is provided with a fitting element 27 which is generally known as a hemostasis valve and which has a generally axial passageway through which the optic fiber bundle 31 may pass. The axial passage is provided with a sealing member coacting with the optic fiber bundle 31 and a side channel. In this manner, a valving arrangement is provided by the hemostasis device. Joined to a side channel of this device is a tube 29 which can be connected to a valve 33 that is joined by way of conduit 34 to a flushing liquid source (not shown).

In a similar manner, guidewire 32 can be pushed into the other channel of the two-channel tubular member 1. The passageway therefor extends from the distal end of the two-channel member 1, through the fork piece 22 including its transitional zone and continues through the single-channel catheter member 24 having connecting member 26 at its proximal end. A fitting element or hemostasis valve device 28 is provided proximal of the connecting member 26 and has an axial channel for guidewire 32 as well as a side channel connected by way of a tube 30 to the flushing liquid source.

By virtue of the uniform transition obtained according to the present invention between both channels 3, 4 of the two-channel catheter member 1 and the channel of each of the single channel tubular members 23, 24, the insertion of the optic fiber bundle 31 and of the guidewire 32 is performed without obstruction or other problems and without irritation being caused during insertion by protruding edges or steps in the fork piece 22, which are avoided in accordance with the present invention. The channel passageway is smooth, and the endoscope fiber can thus be introduced easily without bumping into or engaging rims at transition locations.

Flushing liquid passing through conduit 34 is fed into either or both of the proximal ends of the angioscopy catheter by suitable manipulation of the valve 33. The flushing fluid flows through the angioscopy catheter and exits through distal tip end 36 so that blood is flushed away, including at a location within the vessel distal of the tip end 36, so that the wall of the blood vessel and the like can be examined as soon as the optic fiber bundle 31 is passed out of the end of the catheter and beyond the tip end 36. It will be appreciated the flushing liquid flows through tube 29 and/or 30, into single-channel tubes 23, 24, through the fork piece 22 and through one or both of the longitudinal openings through the two-channel member 1.

In an alternative embodiment, guidewire 31 is provided with a distal end portion 39 which is curved, such as in the illustrated sine shape as shown in FIG. 5. When the distal end portion of the angioscopy catheter is slid along this curved guidewire, the material of the two-channel column will take on a corresponding shape. By turning the angioscopy catheter and guidewire, or by sliding the catheter over the guidewire, the view direction of the optical fiber is changed as needed.

By rotating the guidewire and its associated bent or curved distal end, the tip of the catheter will take on a non-axial movement which can be characterized as a "swivelling around" movement. By this movement, the distal tip end of the optic fiber bundle is provided with different orientations with respect to the axis of the vessel within which it is inserted, with the result that the optic fiber bundle has a characteristic by which it can "look around" in order to enhance the ability of the bundle to inspect and assess the interior of a vessel in a three-dimensional manner. With a curved guidewire end, the catheter will swivel around when the guidewire inserted into the catheter is rotated, whereby the end of the endoscope fiber bundle can be oriented in any direction as desired. The stenosis and the wall of the body vessel into which the catheter is inserted can be accurately examined over its whole periphery. By pushing the guidewire a greater or a lesser distance into the end part of the catheter such as sine-shaped distal tip end 39, the angle at which the end part of the optic fiber bundle lies relative to the longitudinal axis of the catheter also can be varied.

With reference to the procedure or method of use of the invention, the double-lumen angioscopy catheter of the present invention is preferably used in conjunction with a guiding catheter 51 (FIGS. 10–13) having a central channel 52 which has a slightly larger diameter than the outer diameter of the two-channel longitudinal component 1. Preferably, the guiding catheter 51 has a distal tip which has extra radiopaque properties.

Figure 11:
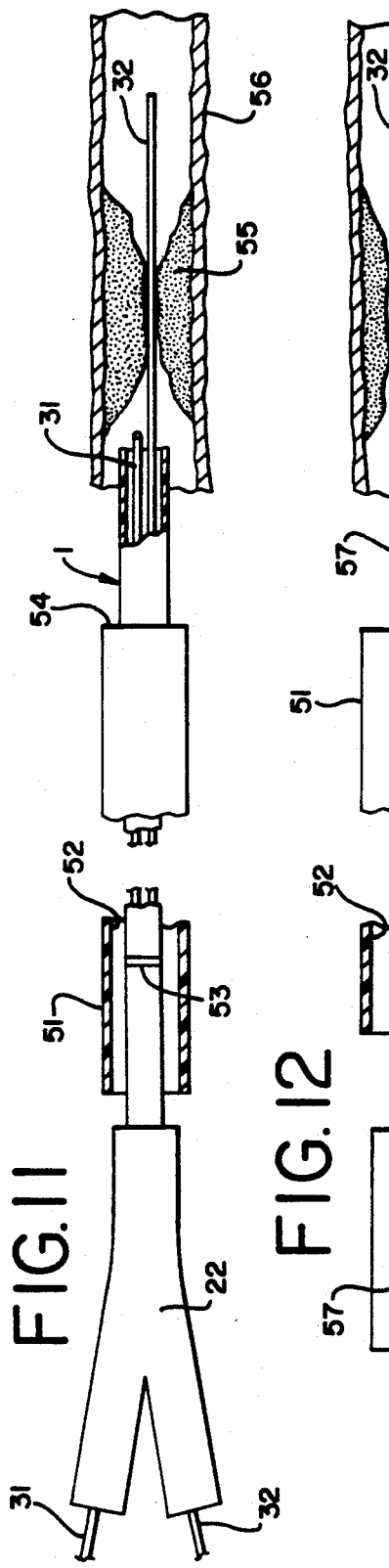
FIG. 11 is a generally schematic view illustrating the use of the double-lumen angioscopy catheter to view a lesion prior to its treatment.

Two-channel member 1 preferably includes a mark 53 such as that illustrated in FIGS. 11 and 14, at a distance from the distal end 36 thereof which is generally equal to the length of the guiding catheter plus any connecting member thereof. At the time that the mark 53 is moved close to the proximal end of the guiding catheter (or any connecting member thereof) during insertion of the double-lumen catheter into the guiding catheter, this will provide a signal to the surgeon or other person administering the treatment that the extremity of the double-lumen catheter is about to leave the distal end 54 of the guiding catheter. For example, in the orientation shown in FIGS. 11 and 13, the mark 53 has moved well within the guiding catheter 51 which indicates that the distal end of the double lumen catheter has projected beyond the distal end 54 of the guiding catheter 51 as shown. Preferably, before introducing the double-lumen angioscopy catheter, the optic fiber bundle 31 will be placed within the catheter such as the distal end of the fiber-bundle 31 and will stay a few millimeters inside the catheter.

By the procedure utilized in connection with the present invention, customary initial insertion steps are performed such as the use of a needle, a mini-guidewire and a sheath introducer which are used in a generally known manner in order to achieve passage of the guiding catheter 51 into the target body pathway to a usual location such as a proximal portion of a coronary vessel. Then, the steerable guidewire 32 is advanced in the coronary vessel. This stage of the procedure is generally illustrated in FIG. 10. It will be noted the distal end of the guidewire 32 has crossed the lesion. If the procedure in accordance with the invention is properly practiced, the lesion is thus crossed only this one time.

It is typically preferred that the double lumen catheter will be used to inspect the lesion 55 or the like within the vessel 56 while also inspecting the inside walls of the vessel 56 itself. The present invention permits this step to be taken through the use of the double lumen angioscopy catheter. During this procedure, the double-channel member 1 thereof is inserted into the patient. Before the catheter is inserted into the patient, the endoscope optic fiber bundle 31 is already arranged within its passageway in the catheter. The distal tip of the guiding catheter preferably is coated with radiopaque material or is otherwise rendered impenetrable by x-ray radiation so that the positioning thereof with respect to the lesion 55 is visible on an x-ray screen in a catheter laboratory. The double-lumen angioscopy catheter is inserted over the guidewire by passing same through the passageway described elsewhere herein which includes the tubular member 24 and its associated pathways. Insertion continues until the double-lumen member 1 is about to exit the guiding catheter 51, which can be indicated by mark 53.

As desired, the double-lumen angioscopy catheter can be advanced, and flushing liquid can be passed through the passageway(s) of the angioscopy catheter, whereby the blood vessel at the leading end of the catheter becomes free of blood or the like, and the lesion and blood vessel wall can be inspected through the optical fiber bundle 31. By such flushing, the vessel at the distal end of the angioscopy catheter will be free of blood, and the optic fiber bundle will provide a clear view inside the vessel. After inspection has been completed as desired, the angioscopy catheter can be removed while the guidewire 32 and guiding catheter 51 remain in place.

Figure 12:
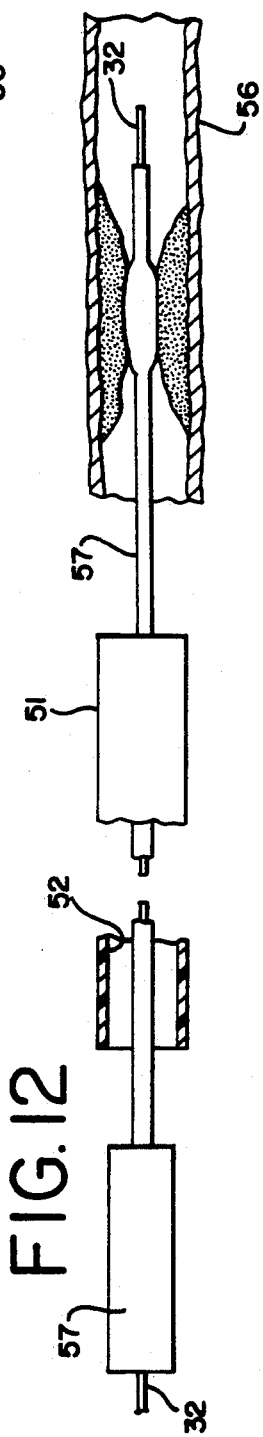
FIG. 12 is a generally schematic view illustrating percutaneous transluminal angioplasty as a component of the procedure of the invention.
Figure 13:
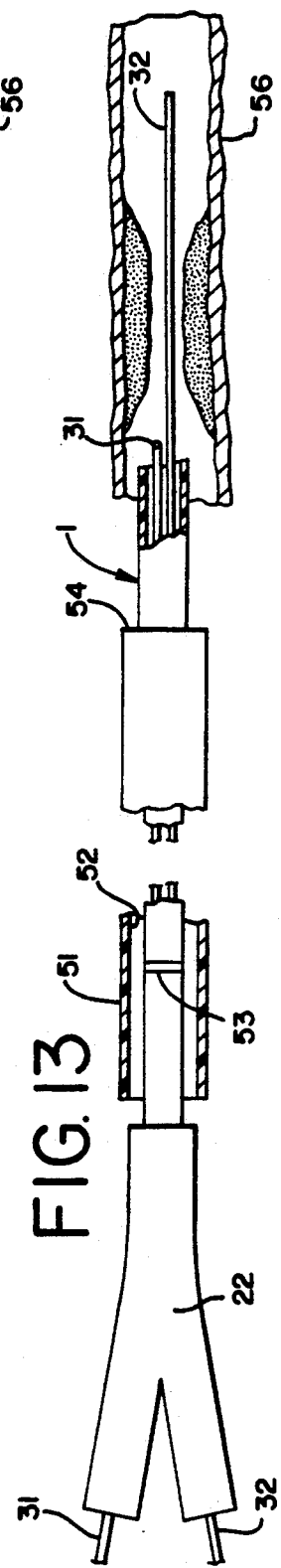
FIG. 13 is a generally schematic view illustrating the procedure wherein the double-lumen angioscopy catheter is used to view a treated lumen.

Thereafter, the device for treating the disease, such as illustrated percutaneous transluminal coronary angioplasty catheter 57, is positioned in accordance with generally known procedures. As shown in FIG. 12, the insertion will be over the guidewire 32 which still remains in place. After the disease treatment has been carried out, the device 57 is removed from the guidewire 32. If desired, the angioscopy catheter can again be inserted over the guidewire 32 in order to be inspect and assess the effectiveness of the treatment. This procedure is illustrated in FIG. 13 and is substantially the same as the inspection procedure described with respect to FIG. 11. After any such post-treatment inspection is carried out, the angioscopy catheter and the guidewire 32 are removed.

By the catheter and procedure in accordance with the present invention, the guidewire remains within the angioscopy catheter during the inspection procedures, and the guidewire does not have to exchanged for the endoscopic fiber bundle 31. In addition, by having the guidewire 32 and the endoscopic optic fiber bundle 31 within the angioscopy catheter at the same time, manipulation of the guidewire can be used for operating the distal end portion of the catheter in a controlled manner in order to control the viewing direction of the endoscope optic fiber bundle 31. In addition, the lumen(s) of the angioscopy catheter can be used as a supply channel for flushing liquid so that it is possible to simultaneously manipulate the catheter and look through the optical fiber bundle 31 of the device.

It will be understood that the embodiments of the present invention which have been described are illustrative of some of the applications of the principles of the present invention. Numerous modifications may be made by those skilled in the art without departing from the true spirit and scope of the invention.

We claim:

1. A double-lumen angioscopy catheter, comprising:
   a length of double-channel tubing having a first longitudinal channel and a second longitudinal channel longitudinally adjacent to said first longitudinal channel, said double-lumen tubing having a distal tip end and a proximal portion;
   a fork member having a distal portion with two passageways therebetween, said fork member having two proximal portion lumens, said two passageways of the distal portion and said two proximal portion lumens communicating with each other through a transitional passageway between said two passageways of the distal protion and said two proximal portion lumens;

each said transitional passageway is substantially devoid of internally protruding edges and has a tapered surface on one of its faces and a generally semi-cylindrical surface on its opposite face, said generally semi-cylindrical opposite face being coextensive both with a generally semi-cylindrical portion of one of said passageways of the distal portion and also with a generally semi-cylindrical portion of one of said proximal portion lumens;

first and second lengths of single-channel tubing each having a lumen concentric with said respective two proximal portion lumens of the fork member;

an endoscopic optic fiber bundle positioned within a first continuous passageway, said first continuous passageway being defined by said first length of single-channel tubing, by one of said proximal portion lumens, by one of said transitional passageways, by one of said proximal passageways within the fork member, and by said first longitudinal channel of the double-channel tubing, said first continuous passageway presenting a continuous length having a generally semi-cylindrical configuration which is constant in shape and size, said continuous length including said generally semi-cylindrical opposite face of its transitional passageway and extending at least throughout said transitional passageway and the proximal portion of said first longitudinal channel of the double-lumen tubing;

a second continuous passageway defined by said second length of single-channel tubing, by the other of said proximal portion lumens, by another of said transitional passageways, by the other of said proximal passageways within the fork member, and by said second longitudinal channel of the double-channel tubing, said second continuous passageway presenting a continuous length having a generally semi-cylindrical configuration which is constant in shape and size, said continuous length including said generally semi-cylindrical opposite face of its transitional passageway and extending at least throughout said transitional passageway and the proximal portion of said second longitudinal channel of the double-lumen tubing; and said second continuous passageway receives a guidewire therewithin.

2. The double-lumen angioscopy catheter according to claim 1, wherein said transitional passageway is shaped and sized to gradually transform said two passageways of the distal portion of the fork member into said two proximal portion lumens of the fork member.

3. The double-lumen angioscopy catheter according to claim 1, wherein the two passageways of the distal portion of the fork member have a generally D-shaped cross-section and the two proximal portion lumens have a generally circular cross-section.

4. The double-lumen angioscopy catheter according to claim 3, wherein each transitional passageway includes a transitional zone which has a tapered surface positioned between the generally D-shaped cross-section and the generally circular cross-section.

5. The double-lumen angioscopy catheter, comprising:

a length of double-channel tubing having a first longitudinal channel and a second longitudinal channel longitudinally adjacent to said first longitudinal channel, said double-lumen tubing having a distal tip end and a proximal portion;

a fork member having a distal portion with two passageways therebetween, said fork member having two proximal portion lumens, said two passageways of the distal portion and said two proximal portion lumens communicating with each other through a transitional passageway between said two passageways of the distal portion and said two proximal portion lumens;

each said transitional passageway is substantially devoid of internally protruding edges and has a tapered surface on one of its faces and a generally semi-cylindrical surface on its opposite face, said generally semi-cylindrical opposite face being coextensive both with a generally semi-cylindrical portion of one of said passageways of the distal portion and also with a generally semi-cylindrical portion of one of said proximal portion lumens;

first and second lengths of single-channel tubing each having a lumen concentric with said respective two proximal portion lumens of the fork member;

an endoscopic optic fiber bundle positioned within a first continuous passageway, said first continuous passageway being defined by said first length of single-channel tubing, by one of said proximal portion lumens, by one of said transitional passageways, by one of said proximal passageways within the fork member, and by said first longitudinal channel of the double-channel tubing, said first continuous passageway presenting a continuous length having a generally semi-cylindrical configuration which is constant in shape and size, said continuous length including said generally semi-cylindrical opposite face of its transitional passageway and extending at least throughout said transitional passageway and the proximal portion of said first longitudinal channel of the double-lumen tubing;

a second continuous passageway defined by said second length of single-channel tubing, by the other of said proximal portion lumens, by another of said transitional passageways, by the other of said proximal passageways within the fork member, and by said second longitudinal channel of the double-channel tubing, said second continuous passageway presenting a continuous length having a generally semi-cylindrical configuration which is constant in shape and size, said continuous length including said generally semi-cylindrical opposite face of its transitional passageway and extending at least throughout said transitional passageway and the proximal portion of said second longitudinal channel of the double-lumen tubing;

said second continuous passageway receives a guidewire therewithin; and a valve at a proximal end of at least one of the first and second lengths of single-channel tubing, said valve having a generally axial passageway through which an elongated member may pass, said valve having a fitting for receiving a flushing liquid and passing the flushing liquid into said length of single-channel tubing and into and through said continuous passageway associated therewith until the flushing liquid exits the distal tip of the double-channel tubing.

6. The double-lumen angioscopy catheter according to claim 1, wherein a guidewire is within said second continuous passageway.

7. The double-lumen angioscopy catheter according to claim 1, wherein a guidewire is within said second continuous passageway, said guidewire having a curved distal end portion with a generally sine-shaped curve.

* * * * *

UNITED STATES PATENT AND TRADEMARK OFFICE
CERTIFICATE OF CORRECTION

PATENT NO. : 5,292,305
DATED : March 8, 1994
INVENTOR(S) : Alexander C. Boudewijn and Gjalt Bosma It is certified that error appears in the above-indentified patent and that said Letters Patent is hereby corrected as shown below:

```
Col. 5, line 31, "Receiving" should read --receiving--.
Col. 7, line 21, "14" should read --13--.
Col. 8, line 28, "to be inspect" should read --to inspect--;
        line 38, "to exchanged" should read --to be
        exchanged--.
```

Signed and Sealed this

Twenty-sixth Day of September, 1995

Attest:

BRUCE LEHMAN

*Attesting Officer*     *Commissioner of Patents and Trademarks*